United States Patent [19]

Kurauchi et al.

[11] Patent Number: 4,971,993

[45] Date of Patent: Nov. 20, 1990

[54] DIPEPTIDE DERIVATIVES AND ANTIHYPERTENSIVE DRUGS CONTAINING THEM

[75] Inventors: Masahiko Kurauchi, Narashino; Chikahiko Eguchi; Shigebumi Hashimoto, both of Yokohama, all of Japan

[73] Assignee: Ajinomoto Co., Inc., Tokyo, Japan

[21] Appl. No.: 240,362

[22] Filed: Sep. 1, 1988

Related U.S. Application Data

[63] Continuation of Ser. No. 823,743, Jan. 29, 1986, abandoned.

[30] Foreign Application Priority Data

Jan. 31, 1985 [JP] Japan .................................. 60-17341

[51] Int. Cl.$^5$ .............................................. A61K 31/40
[52] U.S. Cl. .................................... 514/422; 514/423; 548/518; 548/533; 548/537
[58] Field of Search ........................ 548/533, 537, 518; 514/422, 423

[56] References Cited

U.S. PATENT DOCUMENTS

| | | | |
|---|---|---|---|
| 4,307,110 | 12/1981 | Condon et al. | 548/533 X |
| 4,385,062 | 5/1983 | Ciabatti et al. | 548/533 X |
| 4,431,644 | 2/1984 | Smith et al. | 548/533 X |
| 4,431,645 | 2/1984 | Smith et al. | 548/533 X |
| 4,450,275 | 5/1984 | Arimura et al. | 548/533 X |
| 4,638,010 | 1/1987 | Weller et al. | 548/533 X |
| 4,642,355 | 2/1987 | Nakamura et al. | 548/533 |
| 4,670,420 | 6/1987 | Okamoto et al. | 514/20 |

FOREIGN PATENT DOCUMENTS 623243 4/1963 Belgium .

OTHER PUBLICATIONS

Beecham, J.A.C.S., 79, (1957), pp. 3257-3261.
Beecham, J.A.C.S., 79, (1957), pp. 3262-3263.

Primary Examiner—Joseph Paul Brust
Attorney, Agent, or Firm—Oblon, Spivak, McClelland, Maier & Neustadt

[57] ABSTRACT

There are disclosed dipeptide derivatives represented by the general formula:

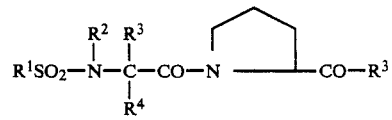

wherein $R^1$ is a radical selected from the group consisting of alkyl, aralkyl and aryl groups optionally containing one or more substituent groups, $R^2$ is a radical selected from the group consisting of hydrogen atoms and alkyl, aralkyl and aryl groups optionally containing one or more substituent groups, $R^3$ is a radical selected from the group consisting of hydrogen atoms and alkyl, aralkyl and aryl groups optionally containing one or more substituent groups, $R^4$ is a radical selected from the group consisting of hydrogen atoms and alkyl, aralkyl and aryl groups optionally containing one or more substituent groups, and $R^5$ is a radical selected from the group consisting of hydroxyl, amino, hydroxyamino, alkyloxy, aralkyloxy, aryloxy, alkylamino, aralkylamino, arylamino, alkyloxyamino, aralkyloxyamino, aryloxyamino, acylamino and sulfonylamino groups, which alkyloxy, aralkyloxy and aryloxy groups optionally containing one or more substituent groups; wherein $R^3$ may be combined with $R^2$ or $R^4$ to form an alkylene bridge optionally containing one or more oxygen atoms, sulfur atoms and nitrogen atoms and optionally containing one or more substituent groups. However, certain dipeptide derivatives within the above general formula are excluded from the invention. The dipeptide derivatives are useful for the treatment of hypertension.

2 Claims, No Drawings

DIPEPTIDE DERIVATIVES AND ANTIHYPERTENSIVE DRUGS CONTAINING THEM

This application is a continuation of application Ser. No. 06/823,743, filed on Jan. 29, 1986, now abandoned.

BACKGROUND OF THE INVENTION

1. Field of the invention

The present invention relates to novel dipeptide derivatives and to antihypertensive drugs containing them.

2. Description of the prior art

Many people suffer from hypertension. The greater the average age of a given group of people, the higher is the rate of hypertension.

Hypertension is also an important factor in cerebral apoplexy and heart disease, which are the second and third highest causes of death. Accordingly, antihypertensive drugs are one of the most important drugs for the treatment of adults.

More than 90 percent of hypertension is essential hypertension, whose cause is unknown. The treatment of this disease is thus limited to the treatment of the symptoms thereof. Therefore, the drugs for this treatment must be safe, efficient and durable.

In recent years, antihypertensive drugs based on amino acids or peptides and acting as inhibitors to angiotensin converting enzyme, have been developed. They are not always satisfactory from the point of view of side effects or durability. Also, most of these drugs consist of a compound having an asymmetric carbon atom in the molecule (excluding the amino acid or peptide portion thereof). Accordingly, an optical resolution is necessary in the synthesis of these compounds, and therefore the synthesizing method is complicated and low in yield.

SUMMARY OF THE INVENTION

The inventors of the present invention have earnestly studied the above problems and have found that the novel proline residue-containing dipeptide derivates represented by the general formula given below have an excellent antihypertensive activity, and that the synthesisthereof is conventional and easy so that they can be easily obtained industrially.

Thus, according to the present invention, there is provided a dipeptide derivative represented by the general formula:

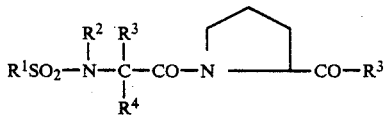

wherein $R^1$ is a radical selected from the group consisting of alkyl cycloalkyl, aralkyl and aryl groups optionally containing one or more substituent groups, $R^2$ is a radicals delected from the group consisting of hydrogen atoms and alkyl cycloalkyl, aralkyl and aryl groups optionally containing one or more substituent groups, $R^3$ is a radical selected from the group consisting of hydrogen atoms and alkyl cycloalkyl, aralkyl and aryl groups optionally containing one or more substituent groups, $R^4$ is a radical selected from the group consisting of hydrogen atoms and alkyl, aralkyl and aryl groups optionally containing one or more substituent groups, and $R^5$ is a radical selected from the group consisting of hydroxyl, amino, hydroxyamino, alkyloxy, aralkyloxy, aryloxy, alkylimino, aralkylamino, arylamino, alkyloxyamino, aralkyloxyamino, arylcxyamino, acylaminc and sulfonylamino groups, which alkyloxy, aralkyloxy and aryloxy groups optionally containing one or more substituent groups; wherein $R^3$ may be combined with $R^2$ or $R^4$ to form an alkylene bridge optionally containing one or more oxygen atoms, sulfur atoms and nitrogen atoms and optionally containing one or more substituent groups; but excluding (A) the derivatives wherein $R^1$ is a 5-(dimethylamino)-1-naphthalenyl group; (B) the derivatives wherein $R^1$ is a 4-methylphenyl group and the group represented by

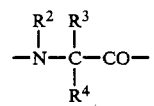

in said general formula is a radical selected from the group consisting of L-pyroglutamic acid and L-glutamic acid radicals; and (C) the derivatives wherein $R^1$ is a group selected from the group consisting of phenyl, 1-naphthalenyl, d-camphoryl, -methoxyphenyl, 4-nitrophenyl and 2,4,6-trimethylphenyl groups, the group represented by

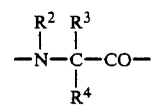

in said general formula is an L-alanine radical, and $R^5$ is a group selected from ethylamino, phenylamino and cyclohexylamino groups.

In the above formula, $R^1$ represents an alkyl, aralkyl or aryl group, which may contain one or more substituent groups, $R^2$, $R^3$ and $R^4$, at least two of which are the same or all of which are different from one another, each individually represents a hydrogen atom, or an alkyl, aralkyl or aryl group, which may have a substituent group, and $R^5$ represents a hydroxyl group, an amino group, a hydroxyamino group, an alkyloxy, aralkyloxy or aryloxy group (which alkyloxy, aralkyloxy or aryloxy groups optionally contain one or more substituent groups), an alkylamino group, an aralkylamino group, an arylamino group, an acylamino group or a sulfonylamino group. Alternatively, $R^2$ and $R^3$ can be combined together to form an alkylene bridge, which optionally contains therein one or more oxygen, sulfur or nitrogen atoms and which optionally contains one or more substituent groups. Similarly $R^3$ and $R^4$ can form an alkylene bridge in the same manner. When the alkylene bridge has a substituent group, examples of the substituent group are hydroxyl group, lower alkoxy group, lower alkyl group, oxo group, condensed aryl group, and condensed alicyclic group.

DESCRIPTION OF THE PREFERRED EMBODIMENTS $R^1$ may be a lower alkyl group having 1 to 6 carbon atoms which may further contain a substituent, for example, methyl, trifluoromethyl, ethyl, n-propyl, isopropyl, n-butyl, isobutyl, sec-butyl, t-butyl, hydroxymethyl, hydroxyethyl, carboxymethyl, carboxyethyl, carbamoylmethyl, carbamoylethyl, aminoethyl, aminopropyl, aminobutyl, guanidinopropyl, imidazolylmethyl, indolylmethyl, mercaptomethyl, mercaptoethyl, benzylthiomethyl, methylthioethyl, dimethylsulfonylethyl, cyclopropyl, cyclobutyl, cyclopentyl, cyclohexyl and cyclooctyl; an aralkyl group having 6 to 12 carbon atoms which may further contain a substituent, for example, benzyl, phenethyl, phenylpropyl, hydroxybenyl, carboxybenzyl, aminobenzyl, nitrobenzyl, fluorobenzyl, chlorobenzyl, bromobenzyl, iodobenzyl, benzyloxybenzyl, and mercaptobenzyl, and aryl group having 6 to 12 carbon atoms which may further contain a substituent, for example, phenyl, naphthyl, anthryl, tolyl, mesityl, biphenyl, hydroxyphenyl, carboxyphenyl, aminophenyl, nitrophenyl, fluorophenyl, pentafluorophenyl, chlorophenyl, bromophenyl, iodophenyl, acetaminophenyl, and mercaptophenyl.

$R^2$ and $R^4$ are the same or different from each other, and each individually may be hydrogen, a lower alkyl group having 1 to 6 carbon atoms which may further contain a substituent, for example, methyl, trifluoromethyl, ethyl, n-propyl, isopropyl, n-butyl, isobutyl, sec-butyl, t-butyl, hydroxymethyl, hydroxyethy-1, carboxymethyl, carboxyethyl, carbamcylmethyl, carbamoylethyl, aminoethyl, aminopropyl, aminobutyl, guanidinopropyl, imidazolylmethyl, indolylmethyl, mercaptomethyl, mercaptoethyl, benzylthiomethyl, methylthioethyl, dimethylsulfonioethyl, cyclopropyl, cyclobutyl, cyclopentyl, cyclohexyl and cyclooctyl; aralkyl group having 6 to 12 carbon atoms which may further contain a substituent, for example, benzyl, phenethyl, phenylpropyl, hydroxybenzyl, carboxybenzyl, aminobenzyl, nitrobenzyl, fluorobenzyl, chlorobenzyl, bromobenzyl, iodobenzyl, benzyloxybenzyl, and mercaptobenzyl; and aryl group having 6 to 12 carbon atoms which may further contain a substituent, for example, phenyl, naphthyl, anthryl, tolyl, mesityl, biphenyl, hydroxyphenyl, carboxyphenyl, aminophenyl, nitrophenyl, fluorophenyl, pentafluorophenyl, chlorophenyl, bromophenyl, idophenyl, acetamidephenyl, and mercaptophenyl.

$R^3$ may be hydrogen, a lower alkyl group having 1 to 6 carbon atoms which may further contain a substituent, for example, methyl, trifluoromethyl, ethyl, n-propyl, isopropyl, n-butyl, isobutyl, sec-butyl, t-butyl, hydroxymethyl, hydroxyethyl, carboxymethyl, carboxyethyl, carbamoylmethyl, carbamoylethyl, aminoethyl, aminopropyl, aminobutyl, guanidinopropyl, imidazolylmethyl, indolylmethyl, mercaptomethyl, mercaptoethyl, benzylthiomethyl, methylthioethyl, dimethylsulfonylethyl, cyclopropyl, cyclobutyl, cyclopentyl, cyclohexyl and cyclooctyl; aralkyl group having 6 to 12 carbon atoms which may further contain a substituent, for example, benzyl, phenethyl, phenylpropyl, hydroxybenzyl, carboxybenzyl, aminobenzyl, nitrobenzyl, fluorobenzyl, chlorobenzyl, bromobenzyl, iodobenzyl, benzyloxybenzyl, and mercaptobenzyl, and aryl group having 6 to 12 carbon atoms which may further contain a substituent, for example, phenyl, naphthyl, anthryl, tolyl, mesityl, biphenyl, hydroxyphenyl, carboxyphenyl, aminophenyl, nitrophenyl, fluorophenyl, pentafluorophenyl, chlorophenyl, bromophenyl, iodophenyl, acetamidephenyl, and mercaptophenyl.

When $R^1$, $R^2$, $R^3$, and/or $R^4$ has a substituent, said substituent is, for example, hydroxy, carboxyl, carbamoyl, amino, guanidino, imidazolyl, indolyl, mercapto group, and lower alkylthio group.

When $R^2$ and $R^3$ are combined together to form the bridge, examples of the structure thereof are as follows:

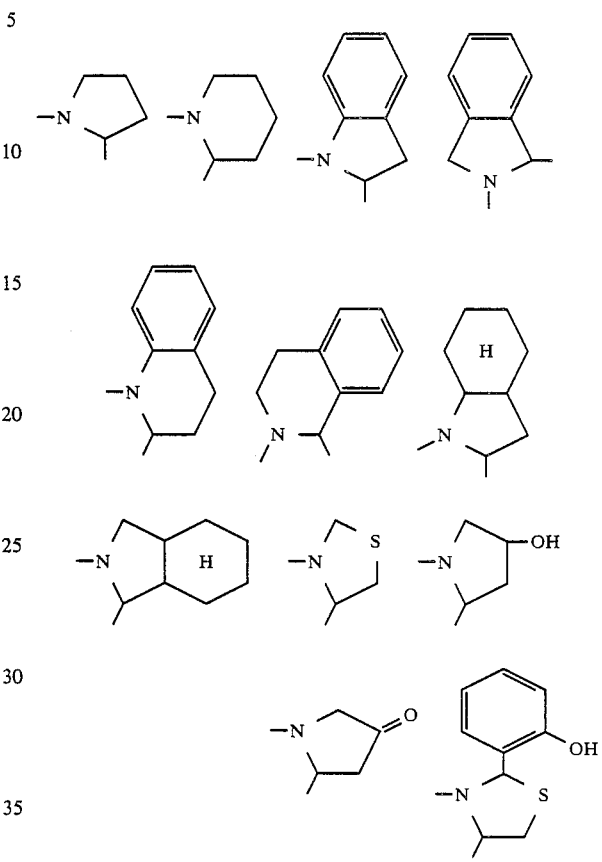

An amino acid constituting the dipeptide derivative of the present invention, may be either the L-isomer or the D-isomer.

The dipeptide derivative of the present invention may be in the form of a salt, such as a metal salt, for example, sodium, potassium, lithium, calcium and barium salts or a salt with an organic base. As the organic base, there can be adopted amines such as ammonia (ammonium salt), dicyclohexylamine, and N-methyl-D-glucamine, procaine, and pyrimidine and basic amino acid such as lysine and arginine.

Of course, when the peptide derivative of the present invention is to be included in the antihypertensive drug of the present invention, it needs to be in a form of a pharmaceutically acceptable salt.

The peptide derivative of the present invention is a derivative wherein alkyl-, aralkyl- or arylsulfonyl group ($RSO_2$) is combined therein in terminal amino group thereof, represented by the formula $RSO_2$—X—Pro wherein X represents amino acid residue, and Pro is proline residue.

Said amino acid is, for example, alanine, arginine, asparagine, aspartic acid, cysteine, glutamine, glutamic acid, glycine, histidine, hydroxyproline, isoleucine, leucine, lysine, methionine, norvaline, norleucine, t-leucine, ornithine, phenylalanine, phenylglycine, serine, threonine, tryptophan, tyrosine, and valine.

The dipeptide derivatives of the present invention are useful as antihypertensive drug for treating hypertensive animals including humans. The derivatives can be used for lowering blood pressure by formularing them into a preparation such as tablets, capsules, and elixirs for oral administration and into an aseptic liquid preparation or an aseptic suspension preparation for parenteral administration. The amino acid derivatives of the present invention can be administered to a subject necessitating such treatment (animals and humans) in a dosage range of 0.2 to 500 mg per subject generally several times a day, that is, in a total daily dosage of 1 to 2000 mg. The dosage varies according to the seriousness of disease, the body weight of subjects, and other factors acknowledged by those skilled in the art.

The dipeptide derivative of the present invention can also be administered together with diuretics or other antihypertensive drugs. Typically, these drugs are administered in a dosage combination of which one unit of daily dose is in the range from one-third as large as a clinical dosage minimally recommended, to a level maximally recommended singly for each entity of disease. These combinations are specially shown as follows: An antihypertensive drug of the present invention which is clinically effective in a daily dosage range of 15 to 200 mg can effectively be administered together with the following other antihypertensive drugs and diuretics in a daily dosage range of 3 to 200 mg: hydrochlorothiazide (15 to 200 mg), chlorothiazide (125 to 2000 mg), ethacrynic acid (15 to 200 mg), amiloride (5 to 20 mg), furosemide (5 to 80 mg), propranolol (20 to 480 mg), timolol (5 to 50 mg), methyldopa (65 to 2000 mg). The foregoing dosage ranges are adjusted on the basis of unit according to the necessity for the possible daily divided dosage. The dosage varies according to the seriousness of disease, the body weight of subject, and other factors acknowledged by those skilled in the art.

The foregoing typical combinations of drugs are formulated into pharmaceutical compositions stated below: About 0.2 to 500 mg of the derivatives of the present invention, pharmaceutically acceptable salt compounds, or mixtures of both are blended into unit dosage forms generally acknowledged or required for the pharmaceutical practice together with pharmaceutically acceptable vehicles, carriers, excipients, binders, antiseptics, stabilizers, flavorings, and sc forth. The amount of each active substance in these compositions or preparations is adjusted in such a way as to give an appropriate dosage of the prescribed range.

Specific materials which can be incorporated into tablets, capsules, and so forth are as follows: A binder such as tragacanth, gum arabic, cornstarch, and gelatin; an excipient such as microcrystalline cellulose; a swelling agent such as cornstarch, pregelatinized starch, and arginic acid; a lubricant such as magnesium stearate; a sweetener such as sucrose, lactose, and saccharin; a flavoring such as peppermint, an oil from Gaulthenia adenothrix Maxim, and cherry. When the unit dosage form of the preparation is a capsule, a liquid carrier such as fatty oil can further be incorporated in the foregoing type materials. Various other materials can be present as a coating material or in order to vary the physical form of unit dosage forms according to other methods. For example, tablet can be coated with shellac and/or sugar. Syrups or elixirs can contain active compounds, sucrose as a sweetener, methyl- and propylparaben as an antiseptic, a coloring agent, a flavoring such as cherry and an organic flavoring.

Aseptic compositions for injection can be formulated according to the usual practice for preparation of pharmaceutical dosage forms, in which practice an active substance is dissolved or suspended in a vehicle such as water for injection; natural vegetable oils such as sesame oil, palm oil, peanut oil, and cotton seed oil; and synthetic fat vehicle such as ethyl oleate. A buffer, an antiseptic, and antioxidant can further be incorporated as occasion demands.

The present invention will be illustrated by the following Examples.

EXAMPLE 1

N-benzenesulfonyl-L-alanyl-L-proline (a) L-alanyl-L-proline

L-proline methylester hydrochloride (16.58 g, 100 mmole) was dissolved in chloroform (300 ml), and triethylamine (10.12 g, 100 mmole), 1-hydroxybenzotriazole (13.51 g, 100 mmole) and N-benzyloxycarbonyl-L-alanine (22.32 g, 100 mmole) were added thereto under cooling to $-15°$ C. and stirring. To the solution, while keeping the temperature to less than 0° C., a chloroform solution of N,N'-dicyclohexylcarbodiimide (20.63 g, 100 mmole) was added dropwise. After that, the mixture was stirred for 2 hours at 0° C. and then overnight at room temperature. The thus precipitated N,N'-dicyclohexylurea was separated by filtration, and the solution was washed with 10% aqueous sodium bicarbonate, water, 1N hydrochloric acid and water in the order given, and dried over anhydrous sodium sulfate. The solvent was distilled off under reduced pressure and to the residue thus obtained 1N sodium hydroxide (150 ml) was added. The mixture was stirred for 3 hours at 30° C. The thus precipitated N,N'-dicyclohexylurea was separated by filtration, and the filtrate was adjusted to pH 2.5 with 6N hydrochloric acid and was extracted twice with chloroform (200 ml). The chloroform layer was dried over anhydrous sodium sulfate, and the solvent was distilled off under reduced pressure. The thus obtained residue was dissolved in 50% methanol (300 ml), and-hydrogen gas was passed through the solution in the presence of 2% palladium-carbon as a catalyst for 2 hours at 40° C. The catalyst was separated by filtration and the solvent was distilled off under reduced pressure The residue thus obtained was recrystallized from water and ethanol to give L-alanyl-L-proline (13.41 g; 72.0%).

NMR spectrum [$D_2O$, Internal standard TSP] ppm 1.50 (t,3H), 1.71–2.50 (m,4H), 3.35–3.75 (m,2H) 4.05 (q,0.6H), 4.12–4.45 (m,1.4H).

TLC [n-butanol:acetic acid:water=4:2:1; ninhydrine] Rf=0.27.

(b) N-benzenesulfonyl-L-alanyl-L-proline

L-alanyl-L-proline (3.72 g, 20 mmole) was dissolved in 1N sodium hydroxide (20 ml), and diethyl ether (5 ml) solution of benzenesulfonylchloride (3.53 g, 20 mmole) was added dropwise thereto while cooling and stirring while keeping the mixture to pH 12 to 13 with 1N sodium hydroxide. After that addition, the mixture was stirred for 3 hours at room temperature Water (40 ml) was added to the solution, and the mixture was washed twice with diethylether. The water layer was filtered and the filtrate thus obtained was adjusted to pH 1.5 with 1N hydrochloric acid while cooling and stirring to precipitate white crystals of N-benzenesulfonyl-L-alanyl-L-proline (yield: (3.68 g, 56.4%).

NMR spectrum [DMSO-$d_6$; Internal standard: TMS] ppm 1.20 (d,3H), 1.65–2.17 (m,4H), 3.18–3.55 (m,2H), 3.80–4.12 (m,2H), 7.08–7.32 (m,1H), 7.32–7.50 (m,3H), 7.60–7.84 (m,2H), 12.16 (br,1H)

TLC [ethyl acetate:methanol=1:1; iodine] Rf=0.44.
Mass spectrum [FAB mode] M+H=327.

EXAMPLE 2

N-mesitylenesulfonyl-L-alanyl-L-proline

L-alanyl-L-proline (1.86 g, 10 mmole) was dissolved in aqueous sodium hydroxide (10 ml)-dioxane (10 ml), and dioxane (5 ml) solution of mesitylenesulfonylchloride (2.19 g, 10 mmole) was added dropwise to the solution while cooling and stirring while keeping pH value thereof to 10 to 11 with 1N aqueous sodium hydroxide. After that; the mixture was stirred further for 2 hours at room temperature. Water (20 ml) was added thereto and the mixture thus obtained was washed with diethyl ether (40 ml). The water layer was filtered and the filtrate thus obtained was adjusted to pH 2.0 with 1N hydrochloric acid while cooling and stirring to precipitate white solid material. The material was dissolved in 0.5N aqueous sodium hydroxide and the solution thus obtained was crystallized by addition of 1N aqueous hydrochloric acid to give N-mesitylenesulfonyl-L-alanyl-L-proline yield: 1.67 g, 45.3%).

NMR spectrum [DMSO-$d_6$; internal standard: TMS] ppm 1.07 (d.,3H), 1.50–2.06 (m,4H), 2.21 (s,3H), 2.51 (s,6H), 2.92–3.55 (m,2H), 3.56–4.02 (m,2H), 6.89 (s,2H), 7.58 (d,1H), 12.22 (s,1H)

TLC [ethyl acetate:methanol=1:1; iodine]Rf=0.41.
Mass spectrum [FAB mode] M+H=369.

EXAMPLE 3

N-p-toluenesulfonyl-L-alanyl-L-proline

L-alanyl-L-proline (1.86 g, 10 mmole) was dissolved in 1N aqueous sodium hydroxide (10 ml)-dioxane (5 ml), and dioxane (5 ml) solution of p-toluenesulfonylchloride (1.91 g, 10 mmole) was added dropwise to the solution while cooling and stirring while keeping pH value thereof to between 10 and 11 with 1N aqueous sodium hydroxide. After that addition, the mixture was stirred further for 2 hours at room temperature. Water (20 ml) was added thereto and washed with diethyl ether (40 ml). The water layer was filtered and the filtrate thus obtained was adjusted to pH 1.5 with 1N aqueous hydrochloric acid while cooling with ice and stirring to precipitate white crystals of N-p-toluenesulfonyl-L-alanyl-L-proline (yield; 3.26 g, 95.8%).

NMR spectrum [DMSO-$d_6$, internal standard TMS] ppm 1.03 (d,3H), 1.62–2.08 (m,4H), 2.36 (s,3H), 3.13–3.55 (m,2H), 3.71–4.17 (m,2H), 7.26 (d,2H), 7.56 (d,2H), 7.75 (d,1H), 12.23 (s,1H).

TLC [ethyl acetate:methanol=1:1; iodine] Rf=0.39.
Mass spectrum [FAB mode] M+H=341.

EXAMPLE 4

N-α-naphthalenesulfonyl-L-alanyl-L-proline

L-alanyl-L-proline (1.86 g, 10 mmole) was dissolved in 1N aqueous sodium hydroxide (10 ml)-dioxane (5 ml), and dioxane (5 ml) solution of α-naphthalenesulfonylchloride (2.26 g, 10 mmole) was added dropwise to the solution while cooling with ice and stirring while keeping pH value thereof to between 10 and 11 with 1N aqueous sodium hydroxide. After the addition, the mixture was stirred further for 2 hours at room temperature. Water (20 ml) was added thereto and the mixture thus obtained was washed with diethyl ether (40 ml). The water layer was filtered and the filtrate thus obtained was adjusted to pH 2.0 with 1N aqueous hydrochloric acid while cooling with ice and stirring and extracted with ethyl acetate (100 ml). The ethyl acetate was washed with 1N aqueous hydrochloric acid (50 ml) and dried over anhydrous magnesium sulfate. The solution was concentrated under reduced pressure and crystallized by cooling with ice to give N-α-naphthalenesulfonyl-L-alanyl-L-proline[yield: 1.77 g, 47.0%).

NMR spectrum [DMSO-$d_6$; internal standard: TMS] ppm 1.03 (d,3H), 1.46–2.05 (m,4H), 3.06–3.46 (m,2H), 3.50–3.70 (m,1H), 3.82–4.20 (m,1H), 7.36–7.72 (m,2H), 7.83–8.35 (m,3H), 8.41–8.70 (m,1H), 12.10 (br,1H)

TLC [ethyl acetate:methanol=1:1; iodine] Rf=0.41.
Mass spectrum [FAB mode] M+H=377.

EXAMPLE 5

N-α-nitrobenzenesulfonyl-L-alanyl-L-proline

L-alanyl-L-proline (3.72 g, 20 mmole) was dissolved in 1N aqueous sodium hydroxide (20 ml)-dioxane (12 ml), and dioxane (8 ml) solution of o-nitrobenzenesulfonylchloride (4.43 g, 20 mmole) was added dropwise to the solution while cooling with ice and stirring while keeping pH value thereof to between 10 and 11 with 1N aqueous sodium hydroxide. After completion of the addition, the mixture was stirred further for 2 hours at room temperature. Water (40 ml) was added thereto and the mixture was washed with two 40 ml portions of diethyl ether. The water layer was filtered and the filtrate thus obtained was adjusted to pH 2.0 with 1N aqueous hydrochloric acid while cooling with ice and stirring and extracted with two 150 ml portions of ethyl acetate. The ethyl acetate layer was washed with 1N aqueous hydrochloric acid (150 ml) and dried over anhydrous magnesium sulfate. The solvent was distilled off under reduced pressure and the residue thus obtained recrystallized from ethyl acetate and diethyl ether to give N-c-nitrobenzenesulfonyl-L-alanyl-L-proline)yield: 3.10 g, 41.7%).

NMR spectrum [DMSO-$d_6$; internal standard: TMS] ppm 1.18 (d,3H), 1.52–2.23 (m,4H), 3.10–3.63 (m,2H), 3.72–3.95 (m,1H), 3.97–4.40 (m,1H), 7.55–8.00 (m,4H), 8.19 (d,1H), 12.18 (s,1H).

TLC [ethyl acetate:methanol=1:1; iodine] Rf=0.33.
Mass spectrum [FAB mode] M+H=372.

EXAMPLE 6

N-o-aminobenzenesulfonyl-L-alanyl-L-proline

N-o-nitrobenzenesulfonyl-L-alanyl-L-proline (1.51 g, 4.1 mmole) was dissolved in ethanol (10 ml) and hydrogen gas was passed through the solution in the presence of 5% palladium-carbon as a catalyst for 3 hours. The catalyst was separated by filtration and the solvent was distilled off under reduced pressure. The residue thus obtained was recrystallized from ethyl acetate, diethyl ether and petroleum ether to give N-o-aminobenzenesulfonyl-L-alanyl-L-proline (yield: 0.75 g, 56.9%).

NMR spectrum [DMSO-$d_6$; internal standard: TMS] ppm 1.07 (d,3H), 1.53–2.16 (m,4H), 3.15–3.53 (m,2H), 3.70–4.18 (m,2H), 5.82 (s,1H), 6.30–6.88 (m,2H), 7.00–7.50 (m,2H), 7.70 (br,1H).

TLC [ethyl acetate:methanol=1:1; ninhydrine] Rf=0.41.
Mass spectrum [FAB mode] M+H=342.

EXAMPLE 7

N-benzylsulfonyl-L-alanyl-L-proline

L-alanyl-L-proline (1.86 g, 10 mmole) was dissolved in 1N aqueous sodium hydroxide (10 ml)-dioxane (3 ml), and dioxane (7 ml) solution of benzylsulfonylchloride (1.91 g, 10 mmole) was added dropwise to the solution while cooling with ice and stirring while keeping pH value thereof to between 10 and 11 using 1N aqueous sodium hydroxide. After completion of the addition, the mixture was further stirred for 2 hours at room temperature. Water (20 ml) was added thereto and the mixture was washed with diethyl ether (40 ml). The water layer was filtered and the filtrate thus obtained was adjusted to pH 1.5 with 1N aqueous hydrochloric acid while cooling with ice and stirring to precipitate N-benzylsulfonyl-L-alanyl-L-proline in a crystalline form[yield: 1.78 g, 52.3%).

NMR spectrum [DMSO-$d_6$; internal standard: TMS] ppm 1.14 (d,3H), 1.60–2.32 (m,4H), 3.05–3.55 (m,2H), 3.61–4.30 (m,2H), 4.20 (s,2H), 7.26 (s,5H), 12.20 ppm acetate:methanol=1:1; iodine] Rf=0.41.

Mass spectrum [FAB mode] M+H=341.

EXAMPLE 8

N-o-carboxybenzenesulfonyl-L-alanyl-L-proline (a) L-alanyl-L-proline benzylester hydrochloride L-proline benzylester hydrochloride (26.5 g, 110 mmole) was dissolved in methylene chloride (300 ml), and triethylamine (11.14 g, 110 mmole), 1-hydroxybenzotriazole (13.51 g, 100 mmole) and N-t-butyloxycarbonyl-L-alanine (18.92 g, 100 mmole) were added thereto while cooling to −15° C. and stirring. To the solution while keeping the temperature to less than 0° C., methylene chloride (100 ml) solution of N-(3-dimethylaminopropyl)-N'-ethylcarbodiimide hydrochloride (21.09 g, 110 mmole) was added dropwise. After completion of the addition, the mixture was stirred for 2 hours at 0° C. and then overnight at room temperature. The solution was washed with 5% aqueous sodium bicarbonate, water, 1N aqueous hydrochloric acid and water in the order given, and dried over anhydrous sodium sulfate. The solvent was distilled off under reduced pressure, and the oily residue thus obtained was dissolved in 4.5N hydrochloric acid in dioxane (100 ml), and stirred for 1 hour. To the solution chloroform and diethyl ether were added, and thereby L-alanyl-L-proline benzylester hydrochloride as a white crystal was precipitated (yield: 27.42 g, 87.7%).

NMR spectrum [D$_2$O, internal standard TSP] ppm 1.40 (d,3H), 1.73–2.47 (m,4H), 3.33–3.84 (m,2H), 4.27 (q,1H), 4.35–4.70 (m,1H), 5.13 (s,2H), 7.37 (s,5H).

TLC [ethyl acetate:methanol=1:1; ninhydrine] Rf=0.28.

(b) o-chlorosulfonyl benzoic acid benzylester o-Benzyloxycarbonylbenzenesulfonic acid sodium salt (3.14 g, 10 mmole) which had been produced from anhydrous o-sulfobenzoic acid (9.21 g, 50 mmole), sodium carbonate (5,30 g, 50 mmole) and benzyl alcohol (25 ml), was dissolved in N,N-dimethylformamide (5 ml), and thionyl chloride (1.31 g, 11 mmole) was added thereto. The mixture was stirred for 30 minutes at 60° C., and poured into water with ice (150 ml), and extracted with methylene chloride (150 ml). The methylene chloride layer was washed with water (50 ml), and dried over anhydrous magnesium sulfate. The solvent was distilled off under reduced pressure and the thus obtained oily o-chlorosulfonyl benzoic acid benzylester was employed for the next reaction without further purification.

(c) N-o-carboxybenzenesulfonyl-L-alanyl-L-proline dibenzylester

L-alanyl-L-proline benzylester hydrochloride (3.13 g, 10 mmole) was dissolved in methylene chloride (60 ml) and triethylamine (1.01 g, 10 mmole) was added thereto with cooling to −20° C. and stirring. Methylene chloride (5 ml) solution of o-chlorosulfonyl benzoic acid benzylester, as produced above, was added dropwise thereto, and then stirred for 2.5 hours at room temperature. The solution was washed with 1N aqueous hydrochloric acid, water, 5% aqueous sodium bicarbonate and water in the order given, and dried over anhydrous magnesium sulfate. The solvent was distilled off under reduced pressure to give N-o-carboxybenzenesulfonyl-L-alanyl-L-proline benzylester in a sticky form (yield: 4.96 g, 90.1%).

NMR spectrum [chloroform-d; Internal standard: TMS] ppm 1.21 (d,3H), 1.61–2.22 (m,4H), 3.20–3.73 (m,2H), 3.96–4.45 (m,2H), 4.97 (d,2H), 5.31 (s,2H), 6.74 (s,1H), 7.07–7.60 (m,12H), 7.63–8.00 (m,2H).

TLC [ethyl acetate:n-hexane=2:1; iodine] Rf=0.66.

(d) N-o-carboxybenzenesulfonyl-L-alanyl-L-proline

N-o-carboxybenzenesulfonyl-L-alanyl-L-proline dibenzylester (4.78 g, 8.7 mmole) was dissolved in methanol (15 ml), and hydrogen gas was passed through the solution in the presence of 5% palladium-carbon (0.5 g) as a catalyst for 4 hours at room temperature. The catalyst was separated by filtration, and the residue obtained by distilling off the solvent under reduced pressure therefrom, was recrystallized from ethyl acetate, diethyl ether, and n-hexane to give N-o-carboxybenzenesulfonyl-L-alanyl-L-proline (yield 2.57 g, 79.9%).

NMR spectrum [DMSO-$d_6$; internal standard: TMS] ppm 1.12 (d,3H), 1.52–2.20 (m,4H), 3.10–3.59 (m,2H), 3.68–4.43 (m,2H), 7.33–7.90 (m,4H), 12.80 (br,1H)

TLC [ethyl acetate:methanol=1:1; iodine] Rf=0.16.

Mass spectrum [FAB mode] M+H=371.

EXAMPLE 9

N-ethansulfonyl-L-alanyl-L-proline (a) L-alanyl-L-proline-t-butylester

Benzyloxycarbonyl-L-alanyl-L-proline (16.02 g, 50 mmole) was dissolved in methylene chloride (100 ml) solution of 98% sulfuric acid (0.5 ml), and isobutene gas was blown into the solution under cooling until the volume of the solution was increased by 50 ml. After standing it for 64 hours at room temperature, the solution was washed with 0.15M sodium carbonate. The methylene chloride layer was further washed with 10% aqueous citric acid, water, 5% aqueous sodium bicarbonate and water in the order given, and dried over anhydrous magnesium sulfate. The solvent was distilled off under reduced pressure and the oily residue thus obtained was dissolved in t-butanol (90 ml). Hydrogen gas was passed through the solution in the presence of 5% palladium-carbon (6.5 g) as a catalyst for 2 hours at room temperature. The catalyst was separated by filtration and the solvent was distilled off under reduced pressure to give colourless oily L-alanyl-L-proline t-butylester (yield: 10.36 g, 85.5%).

NMR spectrum [chloroform-d; internal standard: TMS] ppm 1.28 (d,3H), 1.43 (s,9H), 1.72-2.40 (m,6H), 3.25-3.76 (m,3H), 4.13-4.43 (m,1H).

TLC [ethyl acetate:methanol=1:1; ninhydrine] Rf=0.29.

(b) N-ethanesulfonyl-L-alanyl-L-proline t-butylester

L-alanyl-L-proline t-butylester (2.42 g, 10 mmole) was dissolved in methylene chloride (50 ml), and triethylamine (1.01 g, 10 mmole) was added thereto with cooling to −20° C and stirring. Methylene chloride (5 ml) solution of ethanesulfonylchloride (1.29 g, 10 mmole) was added dropwise to the solution while keeping the temperature thereof to −20° C. and then stirred overnight at room temperature. The solution was washed with 10% aqueous citric acid, water, 5% aqueous sodium bicarbonate and water in the order given, and dried over anhydrous magnesium sulfate. The solvent was distilled off under reduced pressure to give oily residue of N-ethanesulfonyl-L-alanyl-L-proline t-butylester(yield: 1.04 g, 31.1%).

NMR spectrum [chloroform-d; internal standard: TMS] ppm 1.29 (d,3H), 1.40 (t,3H), 1.43 (s,9H), 1.70-2.38 (m,4H), 3.02 (q,2H), 3.35-3.80 (m,2H), 4.03-4.48 (m,2H), 5.42 (d,1H).

TLC [ethyl acetate:n-hexane=2:1; iodine] Rf=0.42.

(c) N-ethanesulfonyl-L-alanyl-proline potassium salt

N-ethanesulfonyl-L-alanyl-L-proline t-butylester was dissolved in 4.5N hydrochloric acid in dioxane (15 ml) solution and stirred for 3 hours. The solvent was distilled 1 off under reduced pressure and the oily residue thus Obtained (0.72 g) was dissolved in 0.5M aqueous potassium bicarbonate (5.2 ml). The solution was washed with diethyl ether and the water layer was freeze-dried to give N-ethanesulfonyl-L-alanyl-L-proline potassium salt(yield: 0.75 g, 79.3%).

NMR spectrum [D20; internal standard: TSP] ppm 1.26 (d,3H), 1.35 (t,3H), 1.71-2.40 (m,4H), 3.12 (q,2H), 3.29-3.80 (m,2H), 4.05-4.47 (m,2H).

TLC [ethyl acetate:methanol:acetic acid=5:5:1; iodine] Rf=0.68.

Mass spectrum [FAB mode] M+H=317.

EXAMPLE 10

N-benzenesulfonylglycyl-L-proline (a) N-t-butyloxycarbonylglycyl-L-proline benzylester N-t-butyloxycarbonylglycine (21.02 g, 120 mmole), L-proline benzylester hydrochloride (29.01 g, 120 mmole) and HOBt (1.62 g, 12 mmole) were dissolved in methylene chloride (400 ml), and triethylamine (12.14 g, 120 mmole) and WSC hydrochloride (23.00 g, 120 mmole) were added to the solution at −30° C. The mixture was stirred for 2 hours at less than 0° C., and then overnight at room temperature. The solution was washed with 5% aqueous sodium bicarbonate (400 ml, twice), 5% aqueous citric acid (400 ml, twice) and water (400 ml) in the order given, and dried over anhydrous magnesium sulfate. The solvent was distilled off under reduced pressure to give N-t-butyloxycarbonylglycyl-l-proline benzylester(yield 42.50 g, 97.7%).

TLC [chloroform:methanol=5:1] Rf=0.78.

(b) Glycyl-L-proline benzylester hydrochloride

N-t-butyloxycarbonylglycyl-L-proline benzylester (18.12 g, 50 mmole) was dissolved in 4N hydrochloric acid in dioxane (220 ml) solution, and stirred for 20 minutes at room temperature. The solvent was distilled off and the residue thus obtained was powdered in diethyl ether to obtain glycyl-L-proline benzylester hydrochloride (yield: 13.21 g; 88.4%).

TLC [n-butanol:acetic acid:pyridine:water=4:1:1:2] Rf=0.78.

(c) N-benzenesulfonylglycyl-L-proline benzylester

Glycyl-L-proline benzylester hydrochloride (1.49 g, 5 mmole) was dissolved in methylene chloride (30 ml), and triethylamine (1.11 g, 11 mmole) was added thereto at −30° C., and then methylene chloride (10 ml) solution of benzenesulfonylchloride (0.86 g, 5 mmole) was added dropwise. The mixture was stirred for 1 hour at less than 0° C, and then for 5 hours at room temperature, and methylene chloride (60 ml) was added. The mixture thus obtained was washed with 5% aqueous sodium bicarbonate (100 ml, twice), 1N aqueous hydrochloric acid (100 ml, twice) and water (100 ml) in the order given, and dried over anhydrous magnesium sulfate. The solvent was distilled under reduced pressure to give N-benzenesulfonylglycyl-L-proline benzylester (yield: 1.91 g, 94.9%).

TLC [ethyl acetate:n-hexane=1:1] Rf=0.27.

(d) N-benzenesulfonylglycyl-L-proline

N-benzenesulfonylglycyl-L-proline benzylester (1.91 g, 4.7 mmole) was dissolved in methanol (6 ml), 1N aqueous sodium hydrochloride (6 ml) was added, and stirred for 3 hours at a temperature between 30° C. and 35° C. Water (20 ml) was added to the solution and the mixture was washed with two 20 ml portions of diethyl ether and then adjusted to pH 1.5 with 1N aqueous hydrochloric acid. The solvent was removed by distillation under reduced pressure and the solid material thus obtained was dispersed in ethyl acetate (50 ml) and the mixture was dried over anhydrous magnesium sulfate. The solvent was distilled off under reduced pressure to give a glassy residue and it was recrystallized from ethyl acetate and petroleum ether to obtain N-benzenesulfonylglycyl-L-proline(yield: 0.67 g, 45.2%).

NMR spectrum [chloroform-d +DMSO-$d_6$, internal standard: TMS] ppm 1.66-2.35 (m,4H), 3.05-3.55 (m,2H), 3.55-3.78 (m,2H), 4.10-4.40 (m,1H), 6.52 (br,1H), 7.15-7.60 (m,3H), 7.65-7.90 (m,2H)

TLC [ethyl acetate:methanol:acetic acid:water=10:10:1:1] Rf=0.74.

Mass spectrum [FAB mode] M+H=313.

EXAMPLE 11

N-benzenesulfonyl-L-valyl-L-proline (a) N-t-butyloxycarbonyl-L-valyl-L-proline benzylester N-t-butyloxycarbonyl-L-valine (8.69 g, 40 mmole), L-proline benzylester hydrochloride (9.67 g, 40 mmole) and HOBt (5.40 g, 40 mmole) were dissolved in methylene chloride (150 ml), and N-methylmorcholine (4.05 g, 40 mmole) and WSC hydrochloride (7.67 g, 40 mmole) were added thereto at −30° C. The mixture was stirred for 2 hours at less than ° C., and then overnight at room temperature, washed with aqueous sodium bicarbonate (150 ml, twice), 5% aqueous citric acid (150 ml, twice) and water (150 ml) in the order given and dried over anhydrous magnesium sulfate. The solvent was distilled off under reduced pressure to obtain N-t-butyloxycarbonyl-L-valyl-L-proline benzylester(yield: 16.32 g, 100%).

TLC [ethyl acetate:n-hexane=1:1] Rf=0.88.

(b) L-valyl-L-proline benzylester hydrochloride

N-t-butyloxycarbonyl-L-valyl-L-proline benzylester (16.32 g, 40 mmole) was dissolved in 4N hydrochloric acid in dioxane (100 ml) solution, and the solution was stirred for 1 hour at room temperature. The solvent was distilled off and the residue thus obtained was powdered in diethyl ether to give L-valyl-L-proline benzylester hydrochloride (yield 10.31 g, 75.6%).

TLC [n-butanol:acetic acid:pyridine:water=4:1:1:2] Rf=0.77.

(c) N-benzenesulfonyl-L-valyl-L-proline benzylester

L-valyl-L-proline benzylester hydrochloride (1.70 g, 5 mmole) was dissolved in methylene chloride (30 ml), and triethylamine (1.11 g, 11 mmole) was added thereto at −30° C. Methylene chloride (10 ml) solution of benzene sulfonyl chloride (0.86 g, 5 mmole) was added dropwise to the solution. The mixture was stirred for 1 hour at less than 0° C., and then for 5 hours at room temperature, and methylene chloride (60 ml) was added thereto. The solution was washed with aqueous 5% sodium bicarbonate (100 ml, twice), 1N aqueous hydrochloric acid (100 ml, twice) and water (100 ml) in the order given and dried over anhydrous magnesium sulfate. The solvent was stilled off under reduced pressure to obtain N-benzenesulfonyl-L-valyl-L-proline benzylester(yield: 2.00 g, 90.0%).

TLC [ethyl acetate:n-hexane=1:1] Rf=0.55.

(d) N-benzenesulfonyl-L-valyl-L-proline

N-benzenesulfonyl-L-valyl-L-proline benzylester 200 g, 4.5 mmole) was dissolved in methanol (40 ml) and water (5 ml) solution of sodium bicarbonate (0.42 g, 5 mmole) was added thereto. Hydrogen gas was passed through the solution in the presence of 5% palladium-carbon as a catalyst for 3 hours. The catalyst was removed by filtration and the filtrate thus obtained was concentrated under reduced pressure. The residue thus obtained was dissolved in water (20 ml), and 1N aqueous hydrochloric acid (10 ml) was added thereto to give white crystals. They were recrystallized from methylene chloride, ethyl acetate and petroleum ether to obtain N-benzenesulfonyl-L-valyl-L-proline (yield: 1 11 g, 69.6%).

NMR spectrum [chloroform-d +DMSO-$d_6$, internal standard: TMS] ppm 0.96 (t,6H), 1.47-2.18 (m,4H), 2.95-3.95 (m,4H), 6.56 (br,1H), 7.22-7.60 (m,3H), 7.60-7.81 (m,2H).

TLC [ethyl acetate methanol:acetic acid:water=10:10:1:1] Rf=0.81.

Mass spectrum [FAB mode] M+H=355.

EXAMPLE 12

N-benzenesulfonyl-L-isoleucy1-L-proline

(a) N-t-butyloxycarbonyl-L-isoleucyl-L-proline benzylester

N-t-butyloxycarbonyl-L-isoleucine ½ hydrate 36.05 g, 150 mmole), L-proline benzylester hydrochloride 36.26 g, 150 mmole) and HOBT (20.26 g, 150 mmole) were dissolved in methylene chloride (500 ml), and triethylamine 18 g, 150 mmole) and WSC hydrochloride (28.76 g, 150 mmole) were added thereto at −30° C. The mixture was stirred for 2 hours at less than 0° C. and then overnight at room temperature, and the solution was washed with 5% aqueous sodium bicarbonate (500 ml, twice), 5% aqueous citric acid (500 ml, twice) and water (508 ml) in the order given, and dried over anhydrous magnesium sulfate. The solvent was distilled off under reduced pressure to give N-t-butyloxycarbonyl-L-isoleucyl-L-proline benzylester(yield: 58.43 g, 93.1%).

TLC[chloroform:methanol=9:1] Rf=0.75.

(b) L-isoleucyl-L-proline benzylester hydrochloride

N-t-butyloxycarbonyl-L-isoleucyl-L-proline benzylester (39.76 g, 95 mmole) was dissolved in 4N hydrochloric acid in dioxane (360 ml), and stirred for 30 minutes at room temperature. The solvent was distilled and the residue thus obtained was powdered in diethyl ether to obtain L-isoleucyl-L-proline benzylester hydrochloride(yield: 31.31 g, 92.9%).

TLC[n-butanol:acetic acid:pyridine:water=4:1:1:2] Rf=0.70.

(c) N-benzenesulfonyl-L-isoleucyl-L-proline benzylester L-isoleucyl-L-proline benzylester hydrochloride (1.77 g, 5 mmole) was dissolved in methylene chloride 30ml), and triethylamine (1.11 g, 11 mmole) was added thereto at −30° C. Methylene chloride (10 ml) solution of benzene sulfonyl chloride (0.86 g, 5 mmole) was added dropwise thereto. The mixture was stirred for 1 hour at than 0° C., and then for 5 hours at room temperature, and methylene dichloride (60 ml) was added thereto. The ion was washed with 5% aqueous sodium carbonate ml, twice), 1N aqueous hydrochloric acid (100 ml, twice) and water (100 ml) in the order given, and dried over anhydrous magnesium sulfate. The solvent was distilled off under reduced pressure to give N-benzenesulfonyl-L-isoleucyl-L-proline benzylester(yield: 1.96 g, 85.5%).

TLC[ethyl acetate:n-hexane=1:1] Rf=0.60.

(d) N-benzenesulfonyl-L-isoleucyl-L-proline

N-benzenesulfonyl-L-isoleucyl-L-proline benzylester (1.96 g, 4.3 mmole) was dissolved in methanol 40 ml ), and water (5 ml) solution of sodium bicarbonate (0.42 g, 5 mmole) was added thereto. Hydrogen gas was passed through the solution in the presence of 5% palladium-carbon as a catalyst for 3 hours. The catalyst was removed by filtration and the filtrate was concentrated under reduced pressure and the residue thus obtained was dissolved in water (20 ml), methylene chloride (100 ml) was added thereto, and at least 1N aqueous hydrochloric acid (10 ml) was added thereto while vigorous stirring. The methylene chloride layer was taken and dried over anhydrous magnesium sulfate. The solvent was distilled off under reduced pressure and the residue thus obtained was recrystallized from ethyl acetate and petroleum ether to give N-benzenesulfonyl-L-isoleucyl-L-proline (yield: 1.16 g, 73.7%).

NMR spectrum [chloroform-d +DMSO-$d_6$, internal standard] ppm 0.83 (t)3H), 0.90 (d,3H), 1.02-2.06 (m,7H), 3.01-3.48 (m,2H), 3.51-3.82 (m,2H), 7.03-7.50 (m,3H), 7.58-7.81 (m,2H).

TLC [ethyl acetate:methanol:acetic acid:water=10:10:1:1] Rf=0.8.

Mass spectrum [FAB mode] M+H=369.

EXAMPLE 13

N-benzenesulfonyl-L-phenylglycyl-L-proline (a) N-benzenesulfonyl-L-phenylglycine L-phenylglycine (4.53 g, 30 mmole) was dissolved aqueous sodium hydroxide (15 ml), and dioxane (10 ml) solution of benzene sulfonyl chloride (5.30 g, 30 mmole) was added dropwise to the solution while keeping pH value of to between 10 and 11 with 2N aqueous sodium hydroxide while cooling with ice and stirring. The mixture was stirred for 1.5 hours at room temperature, and then the solution was washed with two 100 ml portions of diethyl ether. To the water layer ethyl acetate (150 ml) was added and the solution was adjusted to pH 1.5 with 1N aqueous hydrochloric acid while vigorous stirring. The ethyl acetate layer was separated and dried over anhydrous magnesium sulfate. The solvent was distilled off under reduced pressure, and the residue thus obtained was recrystallized from ethyl acetate and petroleum to give N-benzenesulfonyl-L-phenylglycine (yield: 6.45 g, 73.8%).

TLC [ethyl acetate:n-hexane:acetic acid = 10:10:1] Rf = 0.55.

(b) N-benzenesulfonyl-L-phenylgylcyl-L-proline benzylester

N-benzenesulfonyl-L-phenyglycine (1.46 g, 5 mmole), proline benzylester hydrochloride (1.21 g, 5 mmole) and HOBT (0.68 g, 5 mmole) were dissolved in methylene chloride (30 ml), and triethylamine (0.51 g, 5 mmole) and WSC hydrochloride (0.96 g, 5 mmole) were added thereto at −30+ c. The mixture was stirred for 2 hours at less than 0° C. and then overnight at room temperature and methylene chloride (70 ml) was added to the solution. The solution was washed with 5% aqueous sodium bicarbonate (100 ml, twice), 5% aqueous citric acid (100 ml, twice) and water (100 ml) in the order given and dried over anhydrous magnesium sulfate. The solvent was distilled off under reduced pressure to give N-benzenesulfonyl-L-phenylgylcyl-L-proline benzylester (yield; 2.17 g, 90.7%).

TLC [ethyl acetate:n-hexane = 1:1] Rf = 0.58.

(c) N-benzenesulfonyl-L-phenylglycyl-L-proline

N-benzenesulfonyl-L-phenylgylcyl-L-proline benzylester (2.17 g, 4.5 mmole) was dissolved in methanol (40 ml), and water (5 ml) solution of sodium bicarbonate (0.42 g, 5 mmole) was added thereto. Hydrogen gas was passed through the solution in the presence of 5% palladium-carbon as a catalyst for 3 hours. The catalyst was removed by filtration, and the filtrate was concentrated under reduced pressure. The residue thus obtained was dissolved in water (20 ml), and 1N aqueous hydrochloric acid (10 ml) was added thereto to give white crystals. They were recrystallized from methanol, ethyl acetate and petroleum ether to obtain N-benzenesulfonyl-L-phenylglycyl-L-proline (yield: 0.89 g, 50.5%).

NMR spectrum [chloroform-d +DMSO-d$_6$, internal standard: TMS] ppm 1.69–2.15 (m,4H), 2.91–3.55 (m,2H), 3.79–4.11 (m,1H), 4.99 (d,1H), 6.95–7.50 (m,9H), 7.55–7.75 (m,2H)

TLC [ethyl acetate:methanol:acetic acid:water = 10:10:1:1] Rf = 0.86.

Mass spectrum [FAB mode] M+H = 389.

EXAMPLE 14

N-benzenesulfonyl-L-phenylalanyl-L-proline (a) N-t-butyloxycarbonyl-L-phenylalanyl-L-proline benzylester N-t-butyloxycarbonyl-L-phenylalanine (36.54 g, 137.7 mmole), L-proline benzylester hydrochloride (33.84 g, 140 mmole) and HOBT (18.91 g, 140 mmole) were dissolved in methylene chloride (500 ml), and triethylamine (14.17 g, 140 mmole) and WSC hydrochloride (26.40 g, 137.7 mmole) were added thereto at −30° C. The solution was stirred for 2 hours at less than 0° C. and then overnight at room temperature. The solution was washed with 5% aqueous sodium bicarbonate (400 ml, twice), 5% aqueous citric acid (400 ml, twice) and water (400 ml) in the order given, and dried over anhydrous magnesium sulfate. The solvent was distilled off under reduced pressure. The oily residue thus obtained was crystallized from ethyl acetate and n-hexane to give N-t-butyloxycarbonyl-L-phenylalanyl-L-proline benzylester (yield: 51.61 g, 82.8%).

TLC [ethyl acetate:n-hexane = 1:1] Rf = 0.57.

(b) L-phenylalanyl-L-proline.benzylester hydrochloride

N-t-butyloxycarbonyl-L-phenylalanyl-L-proline benzylester (29.87 g, 66 mmole) was dissolved in 4.5N hydrochloric acid in dioxane solution (220 ml), and stirred for 1.5 hours at room temperature. The solvent was distilled off under reduced pressure, and gelatinous solid material thus obtained was dissolved in water (250 ml). The solution was washed with diethyl ether and the water layer was freeze-dried to obtain L-phenylalanyl-L-proline benzylester hydrochloride(yield: 26.53 g, 100%).

TLC [n-butanol:acetic acid:pyridine:water = 4:1:1:2] Rf = 0.80.

(c) N-benzenesulfonyl-L-phenylalanyl-L-proline benzylester

L-phenylalanyl-L-proline benzylester hydrochloride (1.94 g, 5 mmole) was dissolved in methylene chloride (30 ml), and triethylamine (1.11 g, 11 mmole) was added thereto at −30° C. Methylene chloride (10 ml) solution of benzene sulfonyl chloride (0.86 g, 5 mmole) was added dropwise to the solution. The mixture was stirred for 1 hour at less than 0° C., and then for 5 hours at room temperature, and methylene chloride (60 ml) was added thereto. The solution was washed with 5% aqueous sodium bicarbonate (100 ml, twice), 1N aqueous hydrochloric acid (100 ml, twice) and water (100 ml) in the order given, and dried over anhydrous magnesium sulfate. The solvent was distilled off under reduced pressure to give N-benzenesulfonyl-L-phenylalanyl-L-proline benzylester (yield: 2.14 g, 86.9%).

TLC [ethyl acetate:n-hexane = 1:1] Rf = 0.53.

(d) N-benzenesulfonyl-L-phenylalanyl-L-proline

N-benzenesulfonyl-L-phenylalanyl-L-proline benzylester (2.14 g, 4.3 mmole) was dissolved in methanol (40 ml), and water (5 ml) solution of sodium bicarbonate (0.42 g, 5 mmole) was added thereto. Hydrogen gas was passed through the solution in the presence of 5% palladium-carbon as a catalyst for 3 hours. The catalyst was removed by filtration and the solution was concentrated under reduced pressure. The residue thus obtained was dissolved in water (20 ml), and 1N aqueous hydrochloric acid (10 ml) was added thereto to give white crystals. They were recrystallized from ethyl acetate and petroleum ether to obtain N-benzenesulfonyl-L-phenylalanyl-L-proline (yield: 1.22 g, 69.8%).

NMR spectrum [chloroform-d +DMSO-d$_6$, internal standard: TMS] ppm 1.55-2.19 (m,4H), 2.45-3.45 (m,4H), 3.78-4.25 (m,2H), 7.09 (s,5H), 7.19-7.48 (m,3H), 7.48-7.67 (m,2H).

TLC [ethyl acetate:methanol:acetic acid:water=10:10:1:1] Rf=0.80.

Mass spectrum [FAB mode] M+H=403.

EXAMPLE 15

N-benzenesulfonyl-L-methionyl-L-proline (a) N-t-butyloxycarbonyl-L-methionyl-L-proline benzylester N-t-butyloxycarbonyl-L-methionine dicyclohexylamine salt (44.36 g, 103 mmole), L-proline benzylester hydrochloride (2490 g, 103 mmole) and HOBT (13.92 g, 103 mmole) were dissolved in methylene chloride (400 ml), and WSC hydrochloride (19.75 g, 103 mmole) were added thereto at −30C. The mixture was stirred for 2 hours at less than 0° C., N,N-dimethylformamide (100 ml) was added thereto, and stirred further overnight at room temperature. The solution was washed with 5% aqueous sodium bicarbonate (400 ml, twice), 5% aqueous citric acid (400 ml, twice) and water (400 ml) in the order given, and dried over anhydrous magnesium sulfate. The solvent was distilled off under reduced pressure to obtain N-t-butyloxycarbonyl-L-methionyl-L-proline benzylester (yield: 46.27 g, 100%)

TLC [ethyl acetate:n-hexane=2:1] Rf=0.72.

(b) L-methionyl-L-proline benzylester hydrochloride

N-t-butyloxycarbonyl-L-methionyl-L-proline benzylester (30.15 g, 69 mmole) was dissolved in 4N hydrochloric acid in dioxane (250 ml) solution, and stirred for 1 hour at room temperature. The solvent was distilled off and the residue thus obtained was powdered in diethyl ether to obtain L-methionyl-L-proline benzylester hydrochloride (yield: 22.57 g, 87.6%)

TLC [n-butanol:acetic acid:pyridine:water=4:1:1:2] Rf=0.75.

(c) N-benzenesulfonyl-L-methionyl-L-proline benzylester

L-methionyl-L-proline benzylester hydrochloride (1.86 g, 5 mmole) was dissolved in methylene chloride (30 ml), and triethylamine (1.11 g, 11 mmole) was added thereto at −30° C. Methylene chloride (10 ml) solution of benzene sulfonyl chloride (0.86 g, 5 mmole) was added dropwise to the solution. The mixture was stirred for 1 hour at less than 0° C. and then for 5 hours at room temperature, and methylene chloride (60 ml) was added thereto. The solution was washed with 5% aqueous sodium bicarbonate (100 ml, twice), 1N aqueous hydrochloric acid (100 ml, twice) and water (100 ml) in the order given, and dried over anhydrous magnesium sulfate. The solvent was distilled off under reduced pressure to obtain N-benzenesulfonyl-L-methionyl-L-proline benzylester (yield 1.99 g, 83.5%)

TLC [ethyl acetate:n-hexane=1:1] Rf=0.42.

(d) N-benzenesulfonyl-L-methionyl-L-proline

N-benzenesulfonyl-L-methionyl-L-proline benzylester (1.99 g, 4.22 mmole) was dissolved in dioxane (5 ml), and 1N aqueous sodium hydroxide (5 ml) was added thereto, and stirred for 2 hours at a temperature between 30° C. and 35° C. Water (5 ml) was added to the solution, and the solution was further stirred for 3 hours at a temperature between 30° C. and 35° C. Water (100 ml) was added thereto, and the mixture was washed with two 100 ml portions of diethyl ether, and the pH of the solution was adjusted to 1.0 with 1N aqueous hydrochloric acid. The solution was allowed to stand at room temperature to obtain white and needle-like crystals of N-benzenesulfonyl-L-methionyl-L-proline (yield: 0.86 g, 53.3%).

NMR spectrum [chloroform-d +DMSO-d$_6$, internal standard: TMS] ppm 1.66-2.12 (m,6H), 1.97 (s,3H), 2.46 (t,2H), 3.17-3.63 (m,2H), 3.77-4.26 (m,2H), 7.20-7.50 (m,3H), 7.55-7.83 (m,2H).

TLC [ethyl acetate:methanol:acetic acid:water=10:10:1:1] Rf=0.79.

Mass spectrum [FAB mode] M+H=387.

EXAMPLE 16

N-benzenesulfonyl-L-prolyl-L-proline (a) N-t-butyloxycarbonyl-L-prolyl-L-proline benzylester N-t-butyloxycarbonyl-L-proline (32.29 g, 150 mmole), L-proline benzylester hydrochloride (36.26 g, 150 mmole) and HOBT (20.27 g, 150 mmole) were dissolved in methylene chloride (500 ml), and triethylamine (15.18 g, 150 mmole) and WSC hydrochloride (28.76 g, 150 mmole) were added thereto at −30° C. The mixture was stirred for 2 hours at less than 0° C., and then overnight at room temperature. The solution was washed with 5% aqueous sodium bicarbonate (400 mg, twice), 5% aqueous citric acid (400 ml, twice) and water (400 ml) in the order given, and dried over anhydrous magnesium sulfate. The solvent was distilled off under reduced pressure to obtain N-t-butyloxycarbonyl-L-prolyl-L-proline benzylester (yield: 60.70 g, 100%).

TLC [chloroform:methanol=9:1] Rf=0.82.

(b) L-prolyl-L-proline benzylester hydrochloride

N-t-butyloxycarbonyl-L-prolyl-L-proline benzylester (60.70 g, 150 mmole) was dissolved in 4N hydrochloric acid in dioxane (350 ml) solution, and stirred for 1 hour at room temperature. The solution was concentrated under reduced pressure, and diethyl ether was added to the solution while cooling with ice and stirring to obtain L-prolyl-L-proline benzylester hydrochloride (47.80 g, 94.1%).

TLC [n-butanol:acetic acid:pyridine:water=4:1:1:2] Rf=0.71

(c) N-benzenesulfonyl-L-prolyl-L-proline benzylester

L-prolyl-L-proline benzylester hydrochloride (1.69 g, 5 mmole) was dissolved in methylene chloride (30 ml), and triethylamine (1.11 g, 11 mmole) was added thereto at −30° C. Methylene chloride (10 ml) solution of benzene sulfonyl chloride (0.86 g, 5 mmole) was added dropwise to the solution. The mixture was stirred for 1 hour at less than 0° C., and next for 5 hours at room temperature, and methylene chloride (60 ml) was added thereto. The solution was washed with 5% aqueous sodium bicarbonate (100 ml, twice), 1N aqueous hydrochloric acid (100 ml, twice) and water (100 ml) in the order given, and dried over anhydrous magnesium sulfate. The solvent was distilled off under reduced pressure to obtain N-benzenesulfonyl-L-prolyl-L-proline benzylester(yield: 2.17 g, 98.1%)

TLC [ethyl acetate:n-hexane =1:1] Rf=0.27.

(d) N-benzenesulfonyl-L-prolyl-L-proline

N-benzenesulfonyl-L-prolyl-L-proline benzylester (2.17 g, 4.9 mmole) was dissolved in methanol (40 ml), and water (5 ml) solution of sodium bicarbonate (0.42 g, 5 mmole) was added thereto. Hydrogen gas was passed through the solution in the presence of 5% palladium-carbon as a catalyst for 3 hours. The catalyst was removed by filtration, and the solution was concentrated under reduced pressure, and the residue thus obtained was dissolved in water (10 ml). 1N aqueous hydrochloric acid (10 ml) was added to the solution. The white crystals thus obtained were recrystallized from N,N-dimethylformamide, ethyl acetate and petroleum ether to obtain N-benzenesulfonyl-L-prolyl-L-proline (yield 1.08 g, 62.5%).

NMR spectrum [chloroform-d +DMSO-$d_6$, internal standard: TMS] ppm 1.40–2.18 (m,8H), 3.10–3.88 (m,4H), 4.13–4.57 (m,2H), 7.30–7.57 (m,3H), 7.64–7.85 (m,2H).

TLC [ethyl acetate:methanol:acetic acid:water=10:10:1:1] Rf=0.69.

Mass spectrum [FAB mode]M+H=353.

EXAMPLE 17

N-benzenesulfonyl-L-seryl-L-proline (a) N-t-butyloxycarbonyl-L-seryl-L-proline benzylester N-t-butyloxycarbonyl-L-serine (33.86 g, 165 mmole), L-proline benzylester hydrochloride (39.88 g, 165 mmole) and HOBT (22.29 g, 165 mmole) were dissolved in methylene chloride (500 ml), and triethylamine (16.70 g, 5 mmole) and WSC hydrochloride (31.63 g, 165 mmole) were added thereto at −30° C. The mixture was stirred for 2 hours at less than 0° C., and next overnight at room temperature. The solution was washed with 5% aqueous sodium bicarbonate (400 ml, twice), 5% aqueous citric acid (400 ml, twice) and water (400 ml) in the order given, and dried over anhydrous magnesium sulfate. The solvent was distilled off under reduced pressure to produce oily residue. The residue was crystallized from ethyl acetate and n-hexane to obtain N-t-butyloxycarbonyl-L-seryl-L-proline benzylester (yield: 36.09 g, 55.7%).

TLC [ethyl acetate:n-hexane=2:1] Rf=0.33.

(b) L-seryl-L-proline benzylester hydrochloride

N-t-butyloxycarbonyl-L-seryl-L-proline benzylester (33.99 g, 86.6 mmole) was dissolved in 4N hydrochloric acid in dioxane (300 ml) solution, and stirred for 1 hour at room temperature. To the solution, diethyl ether (500 ml) and n-hexane (100ml) were added to give L-seryl-L-proline benzylester hydrochloride (yield: 28.03 g, 98.4%).

TLC [n-butanol:acetic acid:pyridine:water=4:1:1:2] Rf=0.73.

(c) N-benzenesulfonyl-L-seryl-L-proline benzylester

L-seryl-L-proline benzylester hydrochloride (1.64 g, 5 mmole) was dissolved in methylene chloride (30 ml), and triethylamine (1.11 g, 11 mmole) was added thereto at −30° C. Methylene chloride (10 ml) solution of benzene sulfonyl chloride (0.86 g, 5 mmole) was added dropwise thereto. The mixture was stirred for 1 hour at less than 0° C. and then for 5 hours at room temperature, and methylene chloride (60 ml) was added thereto.

The mixture was washed with 5% aqueous sodium bicarbonate (100 ml, twice), 1N aqueous hydrochloric acid (100 ml, twice) and water (100 ml) in the order given, and dried over anhydrous magnesium sulfate. The solvent was distilled off under reduced pressure to obtain N-benzenesulfonyl-L-seryl-L-proline benzylester (yield: 1.96 g, 90.6%).

TLC [ethyl acetate:n-hexane=1:1] Rf=0.14.

(d) N-benzenesulfonyl-L-seryl-L-proline

N-benzenesulfonyl-L-seryl-L-proline benzylester (1.96 g, 4.5 mmole) was dissolved in methanol (40 ml), and water (5 ml) solution of sodium bicarbonate (0.42 g, 5 mmole) was added thereto. Hydrogen gas was passed through the solution in the presence of 5% palladium-carbon as a catalyst for 3 hours. The catalyst was removed by filtration, and the solvent was distilled off under reduced pressure. The residue thus obtained was dissolved in water (20 ml) and 1N aqueous hydrochloric acid (10 ml) was added thereto. The solution was concentrated under reduced pressure to produce solid material, which is a white residue. The residue was dispersed in ethyl acetate (100 ml) and dried over anhydrous magnesium sulfate. The solvent was distilled off under reduced pressure to obtain a white solid. It was recrystallized from ethyl acetate and petroleum to obtain N-benzenesulfonyl-L-seryl-L-proline (yield: 1.31 g, 66.9%).

NMR spectrum [chloroform-d+DMSO-$d_6$, internal standard: TMS] ppm 1.65–2.20 (m,4H), 2.95–3.75 (m,2H), 3.53 (d,2H), 3.83–4.25 (m,2H), 4.97 (br,2H), 6.90–7.22 (m,1H), 7.25–7.51 (m,3H), 7.63–7.83 (m,2H)

TLC [ethyl acetate:methanol:acetic acid:water=10:10:1:1] Rf=0.67.

Mass spectrum [FAB mode] M+H=343.

EXAMPLE 18

N-benzenesulfonyl-L-glutamyl-L-proline benzylester (a) N-t-butyloxycarbonyl-γ-benzyl-L-glutamyl-L-proline benzylester N-t-butyloxycarbonyl-L-benzyl-L-glutamic acid (34.75 g, 103 mmole), L-proline benzylester hydrochloride (24.90 g, 103 mmole) and HOBT (13.92 g, 103 mmcle) were dissolved in methylene chloride (400 ml), and triethylamine (10.42 g, 103 mmole) and WSC hydrochloride (19.75 g, 103 mmole) were added thereto at −30° C. The mixture was stirred for 2 hours at less than 0° C and then overnight at room temperature. The solution was washed with 5% aqueous sodium bicarbonate (400 ml, twice), 5% aqueous citric acid (400 ml, twice) and water (400 ml) in the order given, and dried over anhydrous magnesium sulfate. The solvent was distilled off under reduced pressure to obtain N-t-butyloxycarbonyl-γ-benzyl-L-glutamyl-L-proline benzylester (yield: 51.67 g, 98.5%).

TLC [ethyl acetate:n-hexane=2:1] Rf=0.82.

(b) γ-benzyl-L-glutamyl-L-proline benzylester hydrochloride

N-t-butyloxycarbonyl-γ-benzyl-L-glutamyl-L-proline benzylester (49.84 g, 95 mmole) was dissolved in 4N hydrochloric acid in dioxane (300 ml) solution, and stirred for 1 hour at room temperature. The solvent was distilled off under reduced pressure and the residue thus obtained was dissolved in heated isopropanol (100 ml). To the solution, petroleum ether was added for crystallization and Y-benzyl-L-glutamyl-L-proline benzylester hydrochloride (36.84 g, 84.1%) was obtained.

TLC [n-butanol:acetic acid:pyridine:water=4:1:1:2] Rf=0.79.

(c) N-benzenesulfonyl-γ-benzyl-L-glutamyl-L-proline benzylester

γ-Benzyl-L-glutamyl-L-proline benzylester hydrochloride (2.30 g, 5 mmole) was dissolved in methylene chloride (30 ml), and triethylamine (1.11 g, 11 mole) was added thereto at −30 ° C. Methylene chloride (10 ml) solution of benzene sulfonyl chloride (0.86 g, 5 mmole) was added dropwise thereto. The solution was stirred for 1 hour at less than 0° C., and then for 5 hours at room temperature, and methylene chloride (60 ml) was added thereto. The solution was washed with 55 aqueous sodium bicarbonate (100 ml, twice), 1N aqueous hydrochloric acid (100 ml, twice), and water (100 ml) in the order given, and dried over anhydrous magnesium sulfate. The solvent was distilled off under reduced pressure to give N-benzenesulfonyl-γ-benzyl-L-glutamyl-L-proline benzylester (yield: 2.61 g, 92.4%)

TLC [ethyl acetate:n-hexane=1:1] Rf=0.58.

(d) N-benzenesulfonyl-l-glutamyl-L-proline

N-benzenesulfonyl-γbenzyl-L-glutamyl-L-proline benzylester (2.61 g, 4.6 mmole) was dissolved in methanol (40 ml), and water (5 ml) suspension of sodium bicarbonate (0.84 g, 10 mmole) was added thereto. Hydrogen gas was passed through the solution in the presence of 5% palladium-carbon as a catalyst for 4 hours. The catalyst was removed by filtration, and the solvent was distilled off under reduced pressure, and the residue thus obtained was dissolved in water (30 ml). The mixture was washed with two 30 ml portions of diethyl ether, to the water layer 1N aqueous hydrochloric acid (15 ml) was added, and the solution thus obtained was concentrated under reduced pressure. The white residue thus obtained was dispersed in a mixture (100 ml) of ethyl acetate and methanol (1:1), and the mixture was dried over anhydrous magnesium sulfate. The solvent was distilled off under reduced pressure to obtain white solid. It was recrystallized from methanol, ethyl acetate and petroleum ether to obtain N-benzenesulfonyl-L-glutamyl-L-proline (yield: 1.36 g, 76.5%).

NMR spectrum [chloroform-d+DMSO-d$_6$, internal standard: TMS] ppm 1.35–2.08 (m,6H), 2.12–2.43 (m,2H), 3.13–4.18 (m,4H), 7.25–7.80 (m,5H).

TLC [ethyl acetate:methanol:acetic acid:water=10:10:1:1] Rf=0.68.

Mass spectrum [FAB mode] M+H=385.

EXAMPLE 19

N$^\alpha$-benzenesulfonyl-L-lysyl-L-proline (a) N$^\alpha$-benzenesulfonyl-N$^\epsilon$-benzyloxycarbonyl-L-lysine dicyclohexylamine salt N$^\epsilon$-benzyloxycarbonyl-L-lysine (8.41 g, 30 mmole) was dissolved in 1N aqueous sodium hydroxide (30 ml), and dioxane (10 ml) solution of benzene sulfonyl chloride (5 30 g, 30 mmole) was added dropwise to the solution while keeping the pH value thereof to between 10 and 11 with 1N aqueous sodium hydroxide while cooling with ice and stirring. The mixture was further stirred for 1.5 hours at room temperature and then insoluble matter was removed by filtration. The filtrate was washed with two 100 ml portions of diethyl ether. To the water layer, ethyl acetate (150 ml) was added and the solution was adjusted to pH 1.5 with 1N aqueous hydrochloric acid under vigorous stirring. The ethyl acetate layer was separated and dried over anhydrous magnesium sulfate. The solvent was distilled off under reduced pressure and the oily residue thus obtained was dissolved in acetonitrile (200 ml), and then dicyclohexylamine (5.43 g, 30 mmole) was added thereto with stirring, and thereby N$^\alpha$-benzenesulfonyl-N$^\epsilon$-benzyloxycarbonyl-L-lysine dicyclohexylamine salt (13.21 g, 73.2%) was obtained.

TLC [ethyl acetate:n-hexane:acetic acid=20:10:1] Rf=0.39.

(b) N$^\alpha$-benzenesulfonyl-N$^\epsilon$-benzyloxycarbonyl-L-lysyl-L-proline benzylester N$^\alpha$-benzenesulfonyl-N$^\epsilon$-benzyloxycarbonyl-L-lysine dicyclohexylamine (3.01 g, 5 mmole), proline benzylester hydrochloride (1.21 g, 5 mmole) and HOBT (0.68 g, 5 mmole) were dissolved in methylene chloride (30 ml) and WSC hydrochloride (0.96 g, 5 mmole) was added thereto at −30° C. The mixture was stirred for 2 hours at less than 0° C., and then overnight at room temperature, and methylene chloride (70 ml) was added to the solution. The solution was washed with 5% aqueous sodium bicarbonate (100 ml, twice), 5% aqueous citric acid (100 ml, twice) and water (100 ml) in the order given, and dried over anhydrous magnesium sulfate. The solvent was distilled off under reduced pressure to obtain N$^\alpha$-benzenesulfonyl-N$^\epsilon$-benzyloxycarbonyl-L-lysyl-L-proline benzylester[(yield: 1.68 g. 55.3%).

TLC [ethyl acetate:n-hexane=1:1] Rf=0.30.

(c) N$^\alpha$-benzenesulfonyl-L-lysyl-L-proline

N$^\alpha$-benzenesulfonyl-N$^\epsilon$-benzyloxycarbonyl-L-lysyl-L-proline benzylester (1.68 g, 2.8 mmole) was dissolved in methanol (40 ml), and then hydrogen gas was passed through the solution in the presence of 5% palladium-carbon as a catalyst for 6 hours. The catalyst was removed by filtration, and the solvent was distilled off under reduced pressure. The residue thus obtained was dissolved in water (25 ml). The solution was washed with three 25 ml portions of diethyl ether, and the water layer was freeze-dried to N$^\alpha$-benzenesulfonyl-L-lysyl-L-proline (yield: 0.21 g, 19.8%).

NMR spectrum [D$_2$O, internal standard TSP] ppm 1.05–2.20 (m,10H), 2.70–3.10 (m,2H), 3.17–3.69 (m,3H), 3.85–4.10 (m,1H), 7.67–7.85 (m,5H).

TLC [ethyl acetate:methanol:acetic acid:water=10:10:1:1] Rf=0.16.

Mass spectrum [FAB mode] M+H=384.

EXAMPLE 20

N$^\alpha$-o-aminobenzenesulfonyl-L-lysyl-L-proline (a)

N$^\alpha$-o-nitrobenzenesulfonyl-N$^\epsilon$-benzyloxycarbonyl-L-lysine dicyclohexylamine salt N$^\epsilon$-benzyloxycarbonyl-L-lysine (4.42 g, 16 mmole) was dissolved in 1N aqueous sodium hydroxide (16 ml), and dioxane (10 ml) solution of o-nitrobenzene sulfonyl chloride (3.50 g, 16 mmole) was added dropwise to the solution while keeping the pH value thereof to between 10 and 11 with 1N aqueous sodium hydroxide while cooling with ice and stirring. The mixture was further stirred for 2.5 hours at room temperature, and insoluble matter was removed by filtration. The filtrate thus obtained was washed with two 100 ml portions of diethyl ether. To the water layer, ethyl acetate (150 ml) was added and the solution was adjusted to pH 1.0 with 1N aqueous hydrochloric acid under vigorous stirring. The ethyl acetate layer was separated and dried over anhydrous magnesium sulfate. The solvent was distilled off under reduced pressure and the oily residue thus obtained was dissolved in diethyl ether (50 ml). To the solution, with stirring, dicyclohexylamine 2.99 g, 17 mmole) was added to obtain $N^\alpha$-o-nitrobenzenesulfonyl-$N^\epsilon$-benzyloxycarbonyl-L-lysine dicyclohexylamine salt (yield:8.52 g; 83.4%)

TLC [n-butanol:acetic acid:pyridine:water=4:1:1:2] Rf=0.75.

$N^\alpha$-o-nitrobenzenesulfonyl-$N^\epsilon$-benzyloxycarbonyl-L-lysyl-L-proline benzylester $N^\alpha$-o-nitrobenzenesulfonyl-$N^\epsilon$-benzyloxycarbonyl-L-lysine dicyclohexylamine (6.46 g, 10 mmole), proline benzylester hydrochloride (2.41 g, 10 mmole) and HOBT (1.35 g, 10 mmole) were dissolved in methylene chloride (30 ml), and WSC hydrochloride (1.97 g, 10 mmole) was added thereto at −30° C. The mixture was stirred for 2 hours at less than 0° C., and then overnight at room temperature, and methylene chloride (70 ml) was added to the solution. The solution was washed with 5% aqueous sodium bicarbonate (100 ml, twice), 5% aqueous citric acid (100 ml, twice) and water (100 ml, once) in the order given, and dried over anhydrous magnesium sulfate. The solvent was distilled off under reduced pressure to obtain $N^\alpha$-o-nitrobenzenesulfonyl-$N^\epsilon$-benzyloxycarbonyl-L-lysyl-L-proline benzylester (yield: 5.82 g, 89.2%).

TLC [chloroform:methanol=5:1] Rf=0.90.

(c) $N^\alpha$-o-aminobenzenesulfonyl-L-lysyl-L-proline $N^\alpha$-o-nitrobenzenesulfonyl-$N^\epsilon$-benzyloxycarbonyl-L-lysyl-L-proline benzylester (5.82 g, 8.9 mmole) was dissolved in methanol (40 ml), and hydrogen gas was Passed through the solution in the presence of 5% palladium-carbon as a catalyst for 6 hours. The catalyst was removed by filtration, and the solvent was distilled off under reduced pressure. The residue thus obtained was dissolved in water (25 ml). The solution was washed with three 25 ml portions of diethyl ether and the water layer as separated was freeze-dried to obtain $N^\alpha$-o-aminobenzenesulfonyl-L-lysyl-L-proline (yield: 3.23 g, 90.9%).

NMR spectrum [D$_2$O, internal standard TSP] ppm 1.20–2.20(m,10H), 2.50–2.65(m,2H), 3.10–3.45(m,2H), 3.60–3.90(m,2H) 4.00–5.12(m,4H), 5.77(S,1H), 6.15–7.45(m,4H).

TLC [n-butanol:acetic acid:pyridine:water=4:1:1:2] Rf=0.52.

Mass spectrum [FAB mode] M+H=399.

EXAMPLE 21

2-benzenesulfonylamino isobutyryl-L-proline sodium salt (a) 2-benzenesulfonylaminoisobutyric acid 2-Aminoisobutyric acid (5.16 g, 50 mmole) was dissolved in 2N aqueous sodium hydroxide (25 ml), and dioxane (10 ml) solution of benzene sulfonyl chloride (8.83 g, 50 mmole) was added dropwise to the solution while keeping the pH value thereof to between 10 and 11 with 2N anhydrous sodium hydroxide while cooling with ice and stirring. The mixture was further stirred for 1.5 hours at room temperature. The solution was washed with two 100 ml portions of diethyl ether. To the water layer as separated, methylene chloride (150 ml) was added, and the solution was adjusted to pH 1.5 with 6N aqueous hydrochloric acid under vigorous stirring. The methylene chloride layer was separated and dried over anhydrous magnesium sulfate. The solvent was distilled off under reduced pressure, and the residue thus obtained was recrystallized from ethyl acetate and petroleum ether to obtain 2-benzenesulfonyl aminoisobutyric acid (yield: 7.31 g, 60.0%).

TLC [ethyl acetate:n-hexane:acetic acid=20:10:1] Rf=0.63.

(b) 2-benzenesulfonylamino isobutyryl-L-proline benzylester

2-Benzenesulfonyl aminoisobutyric acid (1.22 g, 5 mmole), proline benzylester hydrochloride (1.21 g, 5 mmole) and HOBT (0.68 g, 5 mmole) were dissolved in methylene chloride (30 ml), and triethylamine (0.51 g, 5 mmole) and WSC hydrochloride (0.96 g, 5 mmole) were added thereto at −30° C. The mixture was stirred for 2 hours at less than 0° C, and then overnight at room temperature, and methylene chloride (70 ml) was added to the solution. The solution was washed with 5% aqueous sodium bicarbonate (100 ml, twice), 5% aqueous citric acid (100 ml, twice) and water (100 ml, once) in the order given, and dried over anhydrous magnesium sulfate. The solvent was distilled off under reduced pressure to obtain 2-benzenesulfonyl aminoisobutyryl-L-proline benzylester[(yield: 1.76 g, 81.8%).

TLC [ethyl acetate:n-hexane=1:1] Rf=0.34.

(c) 2-benzenesulfonyl aminoisobutyryl-L-proline sodium salt

2-Benzenesulfonyl aminoisobutyryl-L-proline benzylester (1.76 g, 4.1 mmole) was dissolved in methanol (40 ml), and water (5 ml) solution of sodium bicarbonate (0.42 g, 5 mmole) was added thereto. Hydrogen gas was passed through the solution in the presence of 5% palladium-carbon as a catalyst for 3 hours. The catalyst was removed by filtration, and the solvent was distilled off under reduced pressure. The residue thus obtained was dissolved in water (30 ml). The solution was washed with two 30 ml portions of diethyl ether, and 1N aqueous hydrochloric acid (10 ml) was added thereto. The solution was concentrated under reduced pressure to a solid residue. The residue was dispersed in methylene chloride (50 ml) and the mixture thus obtained was dried over anhydrous magnesium sulfate. The solvent was distilled off under reduced pressure to obtain an oily residue (0.93 g). It was dissolved in water (20 ml) solution of sodium bicarbonate (0.23 g), and the solution was freeze-dried to obtain a white solid. It was recrystallized from methanol and diethyl ether to obtain 2-benzenesulfonyl aminoisobutyryl-L-proline sodium salt (yield; 0.59 g, 39.8%).

NMR spectrum [D$_2$O, internal standard: TSP] ppm 1.22 (s,3H), 1.41 (s,3H), [isomer's peak (22%) in 1.14 and 1.33], 1.58–2.25 (m,4H), 3.10–4.20 (m,3H), 7.35–7.61 (m,3H), 7.61–7.85 (m,2H).

TLC [ethyl acetate:methanol:acetic acid:water=10:10:1:1] Rf=0.72.

Mass spectrum [FAB mode] M+H=363, M+Na=385.

EXAMPLE 22

The antihypertensive activity of the peptide derivatives as prepared above was determined.

As subject animals there were used 5 SHR which had been trained enough and been confirmed to be hypertensive spontaneously hypertensive rats (male, body weight of 400-440 g),per sample As an instrument for measuring the blood pressure there was used Programmed Electro-Sphygmomanometer PE-300 (Narco Co., U.S.A.), and the blood pressure was indirectly measured on conscious rats.

An aqueous solution of a sample (0.05 mmole/kg) was once force-fed into the stomach by means of a peroal probe. As a control, deionized water was fed to the same animals as above.

The results were shown in Table 1.

TABLE 1

| | Systolic Blood Pressure, mmHg | | | |
|---|---|---|---|---|
| Example No. | Value before Administration | Lowest value after Administration | Hours after Administration | ΔBlood Pressure |
| 1 | 213 | 185 | 8 | −28 |
| 2 | 202 | 191 | 7 | −11 |
| 3 | 206 | 194 | 7 | −12 |
| 4 | 198 | 185 | 7 | −13 |
| 5 | 211 | 193 | 7 | −18 |
| 6 | 232 | 197 | 7 | −35 |
| 7 | 215 | 194 | 7 | −21 |
| 8 | 203 | 194 | 7 | −9 |
| 9 | 218 | 213 | 7 | −5 |
| 10 | 210 | 201 | 7 | −9 |
| 11 | 214 | 203 | 7 | −11 |
| 12 | 212 | 191 | 7 | −21 |
| 13 | 212 | 204 | 7 | −8 |
| 14 | 219 | 201 | 7 | −18 |
| 15 | 219 | 206 | 4 | −13 |
| 16 | 216 | 195 | 7 | −21 |
| 17 | 216 | 194 | 7 | −22 |
| 18 | 203 | 189 | 7 | −14 |
| 19 | 219 | 191 | 7 | −28 |
| 21 | 210 | 193 | 7 | −17 |

As understood from the above results and explanations, the dipeptide derivatives of the present invention show excellent antihypertensive activity, and therefore can be used as antihypertensive drugs.

We claim:

1. A method of treating hypertension, comprising: administering to a subject an antihypertensive effective amount of the dipeptide compound of the formula:

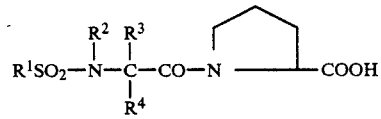

where in $R_1$ is a radical selected from the group consisting of phenyl, mesityl, p-methylphenyl, α-naphthyl, o-nitrophenyl, o-aminophenyl, benzyl, o-carboxyphenyl and ethyl; and radical

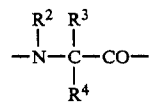

is an amino acid residue selected from the group consisting of L-alanine, L-valine, L-isoleucine, L-phenylalanine, L-methionine, L-serine, L-phenylglycine, L-proline, L-lysine and α,α-dimethylglycine; or a pharmaceutically acceptable salt thereof.

2. A method of treating hypertension, comprising: administering to a subject an antihypertensive effective amount of a compound selected from the group consisting of N-benzenesulfonyl-L-alanyl-L-proline, N-mesitylenesulfonyl-L-alanyl-L-proline, N-p-toluenesulfonyl-L-alanyl-L-proline, N-α-naphthalenesulfonyl-L-alanyl-L-proline, N-o-nitrobenzenesulfonyl-L-alanyl-L-proline, N-o-aminobenzenesulfonyl-L-alanyl-L-proline, N-benzylsulfonyl-L-alanyl-L-proline, N-o-carboxybenzenesulfonyl-L-alanyl-L-proline, N-ethanesulfonyl-L-alanyl-L-proline, N-benzenesulfonylglycyl-L-proline, N-benzenesulfonyl-L-valyl-L-proline, N-benzenesulfonyl-L-isoleucyl-L-proline, N-benzenesulfonyl-L-phenylglycyl-L-proline, N-benzenesulfonyl-L-phenylalanyl-L-proline, N-benzenesulfonyl-L-methionyl-L-proline, N-benzenesulfonyl-L-prolyl-L-proline, N-benzenesulfonyl-L-seryl-L-proline, N-benzenesulfonyl-L-glutamyl-L-proline, $N^\alpha$-benzenesulfonyl-L-lysyl-L-proline, $N^\alpha$-o-aminobenzenesulfonyl-L-lysyl-L-proline, and 2-benzenesulfonylaminoisobutyryl-L-proline; or a pharmaceutically acceptable salt thereof.

* * * * *